(12) United States Patent
Leibowitz

(10) Patent No.: US 9,949,863 B2
(45) Date of Patent: Apr. 24, 2018

(54) POST SURGICAL PROCEDURE UNDERGARMENT

(71) Applicant: Michele Leibowitz, Succasunna, NJ (US)

(72) Inventor: Michele Leibowitz, Succasunna, NJ (US)

( * ) Notice: Subject to any disclaimer, the term of this patent is extended or adjusted under 35 U.S.C. 154(b) by 252 days.

(21) Appl. No.: 14/944,567

(22) Filed: Nov. 18, 2015

(65) Prior Publication Data

US 2017/0135847 A1    May 18, 2017

(51) Int. Cl.
| | |
|---|---|
| *A61F 5/44* | (2006.01) |
| *A41C 3/00* | (2006.01) |
| *A41C 3/04* | (2006.01) |
| *A61F 5/03* | (2006.01) |
| *A61F 13/14* | (2006.01) |

(52) U.S. Cl.
CPC .......... *A61F 5/4408* (2013.01); *A41C 3/0064* (2013.01); *A41C 3/04* (2013.01); *A61F 5/03* (2013.01); *A61F 13/145* (2013.01)

(58) Field of Classification Search
CPC ....... A41C 3/00; A41C 3/0057; A41C 3/0028; A41C 3/006402; A41C 1/006; A41C 1/06; A41C 1/02; A41C 1/00; A41B 9/00
USPC ....... 450/58, 79, 1, 3, 17, 23, 26, 28, 70, 86
See application file for complete search history.

(56) References Cited

U.S. PATENT DOCUMENTS

| | | | |
|---|---|---|---|
| 3,701,168 A | 10/1972 | Balow | |
| 3,950,792 A | 4/1976 | Williams | |
| 4,538,614 A * | 9/1985 | Henderson | A41C 3/0057 2/1 |
| 6,390,885 B1 | 5/2002 | Brooks | |
| D466,673 S | 12/2002 | Furlong | |
| 8,465,341 B2 | 6/2013 | Shashy | |
| 8,808,056 B2 | 8/2014 | Murphy et al. | |
| 2002/0121273 A1 | 9/2002 | Nyilas | |
| 2006/0173427 A1* | 8/2006 | Urbina | A41C 3/0064 604/327 |
| 2011/0230863 A1 | 9/2011 | Lentini | |

(Continued)

OTHER PUBLICATIONS

International Search Report and Written Opinion dated Mar. 13, 2017 in International Patent Application No. PCT/US2016/061803 (17 pages).

(Continued)

*Primary Examiner* — Gloria Hale
(74) *Attorney, Agent, or Firm* — Fox Rothschild LLP

(57) ABSTRACT

An undergarment including a main body having a back panel and a pair of front panels extending from opposite sides of the back panel with the front panels interconnectable to one another such that the main body defines a continuous structure. A pair of shoulder straps extend from an upper edge of the main body with each shoulder strap including a rear strap portion and a front strap portion which are interconnectable to one another such that the shoulder straps define an arm hole on each side of the undergarment. Each armhole has a lowermost point along the main body. An underbust band extends along a lower edge of the main body. Each strap front portion has a length from a free end thereof to the lowermost point which is approximately equal to a total height defined by a height of the main body at the lowermost point plus a height of the underbust band.

13 Claims, 4 Drawing Sheets

(56) References Cited

U.S. PATENT DOCUMENTS

| | | | |
|---|---|---|---|
| 2013/0017760 A1 | 1/2013 | Kadium | |
| 2013/0171911 A1* | 7/2013 | Swendseid | A41C 3/0028 |
| | | | 450/85 |
| 2013/0252512 A1 | 9/2013 | Haley | |
| 2014/0031775 A1 | 1/2014 | Criss | |
| 2014/0302748 A1* | 10/2014 | Blackwell | A41C 3/0064 |
| | | | 450/58 |
| 2015/0099420 A1 | 4/2015 | Reinhard | |

OTHER PUBLICATIONS

Amoena Patricia Zip Front Compression Bra [Style No. AM-2863 by Amoena Mastectomy[ dated Jun. 1, 2014 at www.studioeurope.com/au/amoena-mastectomy-patricia-compression-bra.html (3 pages).

Amoena Theraport Radiation Therapy Garment (2161) dated Jun. 1, 2014 at www.ppcarewear.com/amonena/amonena-theraport-radiation-therapy-garment-2161 (1 page).

Step 2 [after your surgery], Just Call Us, Mastectomy Garments After Your Surgery, Halifax, NS, dated Jun. 1, 2014 at www.justcallushealthsolutions.ca/step-2-after-your-surgery (5 pages).

Wear East Post-Mastectomy, Breast Augmentation/Reduction Compression Bra (w/2 Removable Drain Tube Pouches) dated Jun. 1, 2014 at www.makemeheal.com/mmh/product.do?id=11732 (4 pages).

98 Trulife Chelsea Mastectomy Bra from Jun. 1, 2014, www.contourmd.com/98-Camp-Trulife-Chelsea-Mastectomy-Bra (3 pages).

\* cited by examiner

POST SURGICAL PROCEDURE UNDERGARMENT

FIELD OF THE INVENTION

The present invention relates generally to surgical appliances and supplies and, more specifically, to a garment worn by women who have undergone breast surgeries.

BACKGROUND OF THE INVENTION

Each year, thousands of women undergo breast surgery. Of all the surgeries that a woman may experience, breast surgery, and particularly mastectomy or removal of a breast or breasts, is the most traumatic. A mastectomy is the most common surgical procedure performed when a malignant tumor is found. The type of surgery depends upon the staging of the tumor and the client's preferences. Although many women look for more conservative treatment and less destructive surgery than removal of the breast, mastectomy continues to be the preferred course of treatment to increase the likelihood of destroying the breast cancer. Mastectomy procedures include modified radical mastectomy (removal of the underlying muscle as well as the breast), simple mastectomy (removal of one breast), bilateral mastectomy (removal of both breasts) and lumpectomy (removal of a portion of the breast).

When the cancer involves the muscle or interpectoral node, substantially more muscle and tissue must be removed. Removal of auxiliary nodes and lymphatic channels predisposes the client to infection and lymphatic obstruction. Edema, an abnormal excess accumulation of serious fluid in connective tissue, is a frequent occurrence in breast surgeries unless positive steps are taken to prevent it. The body develops a collateral lymphatic drainage system usually within 3 to 4 weeks postoperatively. In the interim, lymphatic fluid production must be drained to prevent infection and promote healing.

Post-operative drainage tubes are placed in the body to aid in lymphatic fluid drainage. Drainage tube systems are used not only for mastectomies but also for breast reconstructive surgery as well as for less radical surgeries for breast enlargement or breast reduction. The drainage tube system conventionally consists of one to two flexible tubes which exit the chest wall on one or both sides of the body in the area of the incision wound. The drainage tubes extend outside the body and a collection bulb or cup is installed on the end of the drainage tube to collect lymphatic fluids and tissue debris. The drainage tubes and collection bulbs are conventionally gathered together and pinned to the front of the patient's gown with a safety pin. The collection bulb must be emptied of lymphatic discharge on a regular basis, approximately every hour to promote free flow of discharge. The entire drainage system must be supported to prevent pain and inflammation resulting from the disruption and separation of the tubes from the chest wall.

Additionally, it is important that while the undergarment is functional in providing necessary support and drainage functionality, the undergarment should minimize discomfort to the incisions and tender tissue of the patient.

SUMMARY OF THE INVENTION

In at least one embodiment, the present invention provides an undergarment which may be used for various breast surgeries including any breast augmentation surgery, mastectomy surgery, or lumpectomy surgery.

In at least one embodiment, the present invention provides an undergarment including a main body having a back panel and a pair of front panels extending from opposite sides of the back panel with the front panels interconnectable to one another such that the main body defines a continuous structure. A pair of shoulder straps extend from an upper edge of the main body with each shoulder strap including a rear strap portion and a front strap portion which are interconnectable to one another such that the shoulder straps define an arm hole on each side of the undergarment. Each armhole has a lowermost point along the main body. An underbust band extends along a lower edge of the main body. Each strap front portion has a length from a free end thereof to the lowermost point which is approximately equal to a total height defined by a height of the main body at the lowermost point plus a height of the underbust band.

In at least one embodiment, the present invention provides an undergarment including a main body having a back panel and a pair of front panels extending from opposite sides of the back panel with the front panels interconnectable to one another such that the main body defines a continuous structure. A pair of shoulder straps extend from an upper edge of the main body such that each shoulder strap defines an arm hole on each side of the undergarment. An underbust band extends along a lower edge of the main body with one or more pouch connectors extending therealong. At least one drain pouch defining a chamber configured to receive a drain bulb or cup and has a connector configured for connection to the one or more pouch connectors.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION OF THE INVENTION

Figure 1:
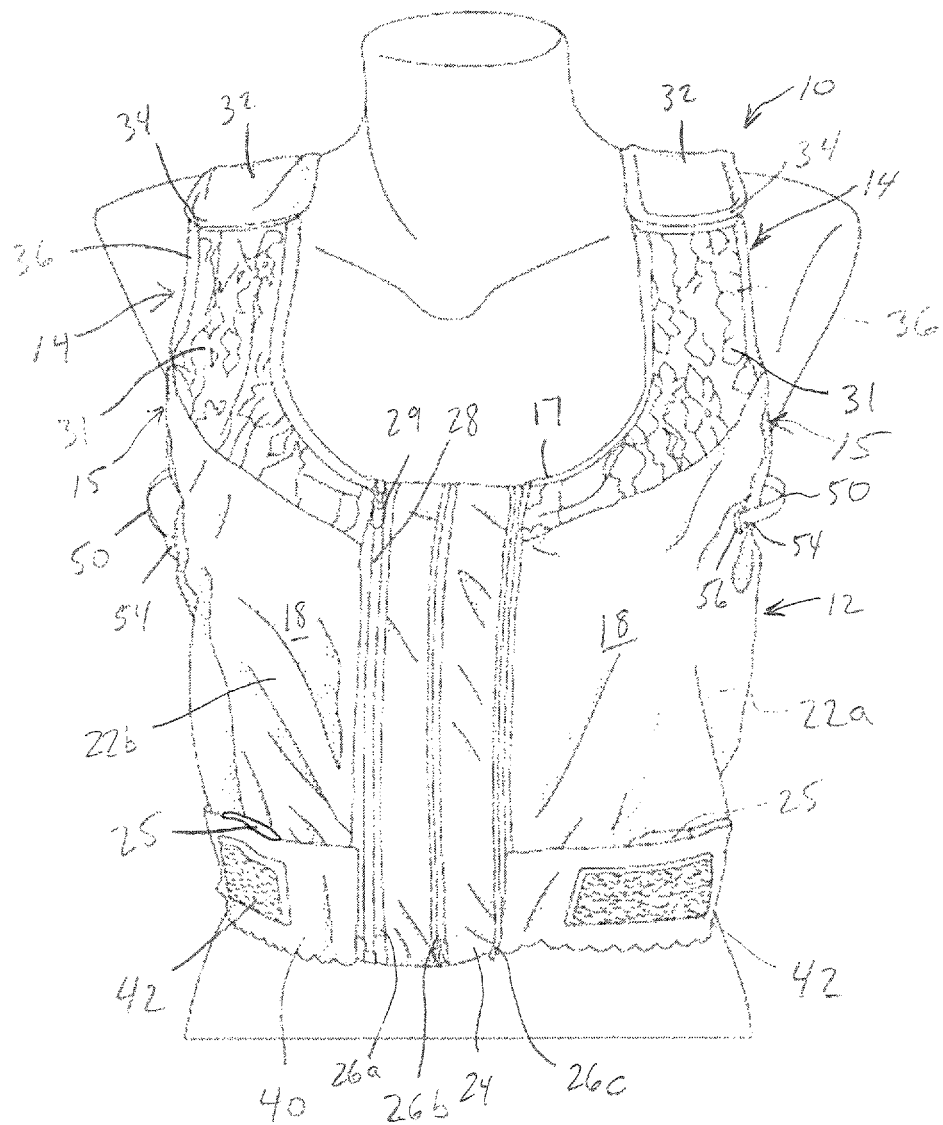
FIG. 1 is a front perspective view of an undergarment in accordance with an embodiment of the invention positioned on a mannequin.

In the drawings, like numerals indicate like elements throughout. Certain terminology is used herein for convenience only and is not to be taken as a limitation on the present invention. The following describes preferred embodiments of the present invention. However, it should be understood, based on this disclosure, that the invention is not limited by the preferred embodiments described herein.

Referring to FIGS. 1-6, an undergarment 10 in accordance with an embodiment of the invention will be described. The undergarment 10 generally includes a main body 12 extending between a pair of upper shoulder straps 14 and a lower underbust band 40. An armhole 15 is defined by each shoulder strap 14 and the respective portion of the main body 12. Additionally, a neckline 17 is defined between the shoulder straps 14 and is bordered by a portion of the main body 12. The configurations of the armholes 15 and neckline 17 will be described in more detail hereinafter.

The main body 12 includes a back panel 20 and a pair of front panels 22a, 22b connected on respective sides of the back panel 20 along seems 21. While the back panel and front panels are illustrated and described as separate, interconnected components, it is recognized that the components may be manufactured as a unitary structure or may comprise more than the three illustrated components, for example, a two-piece back panel. Each front panel 22a, 22b defines a respective bust area 18 which aligns with the wearer's bust when positioned on the patient. In one embodiment, breast flaps (not shown) are defined in the front panels 22a, 22b, to use the undergarment 10, for example, as a nursing bra. The breast flaps can be help by hook and loop fastener or the like.

To secure the main body 12 about the wearer, a connection placket 24 is connected to the front panel 22a and in the illustrated embodiment supports three zipper halves 26a, 26b, and 26c each with a male connector 27. The other front panel 22b supports a zipper half 28 with a female connector 29. Engagement of the female connector 29 with one of the male connectors 27 and mating of the zipper halves facilitates joining of the two front panels 22a and 22b. The multiple zipper halves 26a-26c gives the wearer and the doctor flexibility and the ability to adjust the undergarment 10 to fit during the various phases of swelling, following the surgery. While three zipper halves 26a-26c are illustrated, more or less may be utilized. Additionally, while the present embodiment includes a zippered interconnection, it is recognized that other connectors may be utilized, for example, snaps, hooks, or hook and loop fasteners.

The panels 20, 22a, 22b are preferably manufactured from a breathable fabric with wicking for comfort and to keep patient and wound dry and comfortable while healing. The fabric preferably is preferably elastomeric such that the main body 12 provides a desired level of compression while healing. The connection placket 24 may be made from the same material or different material. In one embodiment, the connection placket 24 is made from a material having a higher elasticity than the material of the panels 20, 22a, 22b to provide greater flexibility in interconnecting the front panels 22a, 22b.

Figure 5:
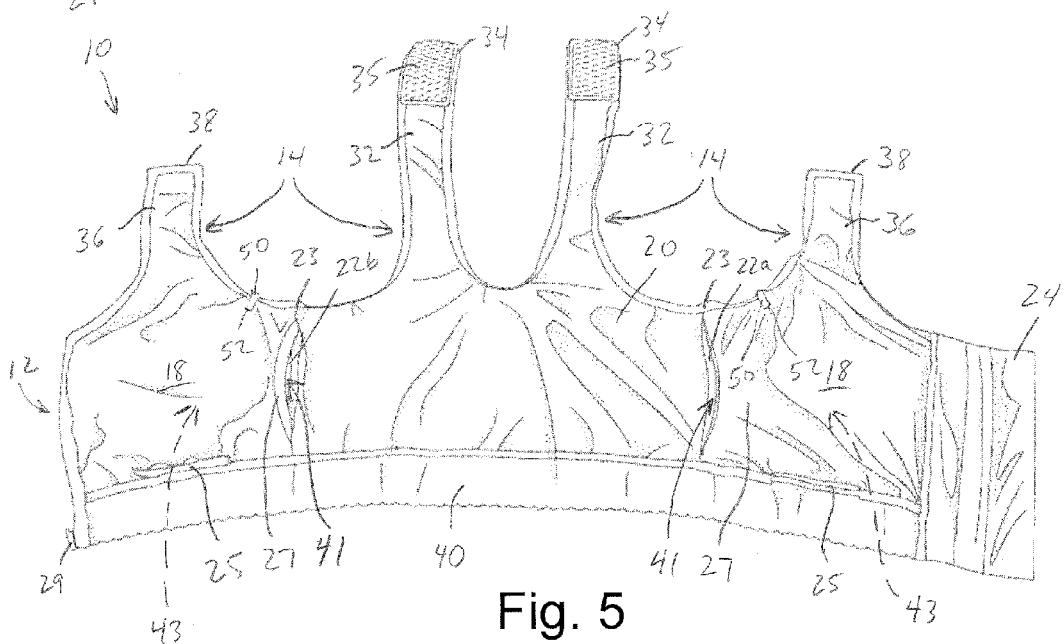
FIG. 5 is a rear elevation view of the undergarment of FIG. 1.
Figure 6:
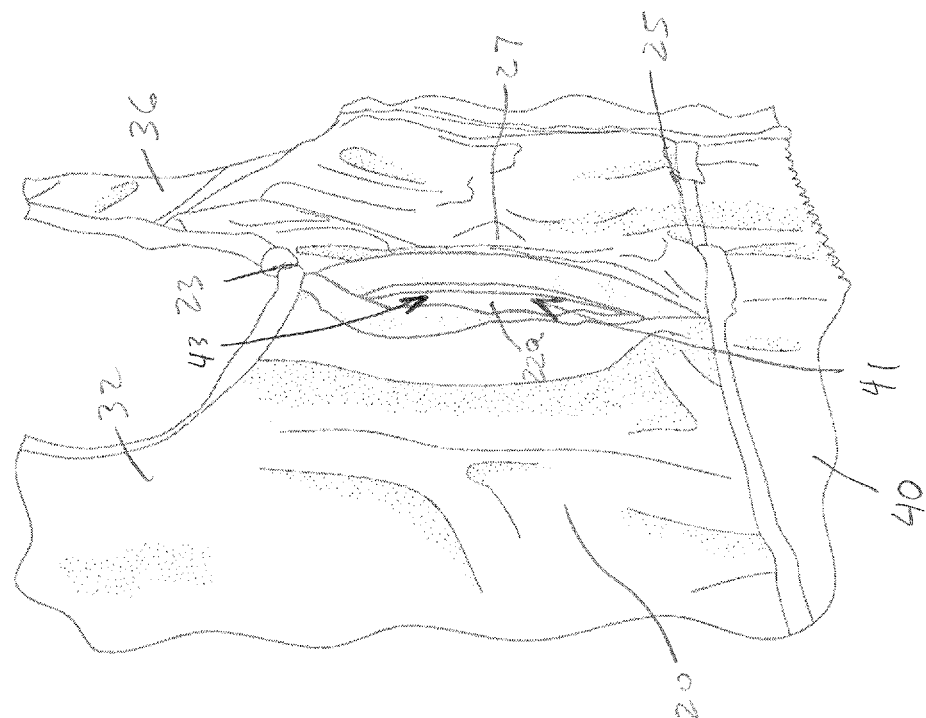
FIG. 6 is a view along a portion of the interior surface of the undergarment of FIG. 1 illustrating an internal pocket in more detail.

Referring to FIGS. 5 and 6, in the illustrated embodiment, the inside of each front panel 22a, 22b includes a secondary panel 27 secured to the respective front panel 22a, 22b except at an area which defines an opening 41 into a respective inside pocket 43 defined between the front panel 22a, 22b and the secondary panel 27. Each inside pocket 43 is aligned with a respective bust area 18 and is configured to hold a prosthetic, ice pack or the like (not shown). The inside pockets 43 may include a temporary closure, for example, hook and loop fasteners, or may be sewn closed. In one embodiment, the inside pockets 43 may be filled with cool pack material and sewn closed so that the undergarment 10 may be put in freezer and used to help swelling.

Figure 2:
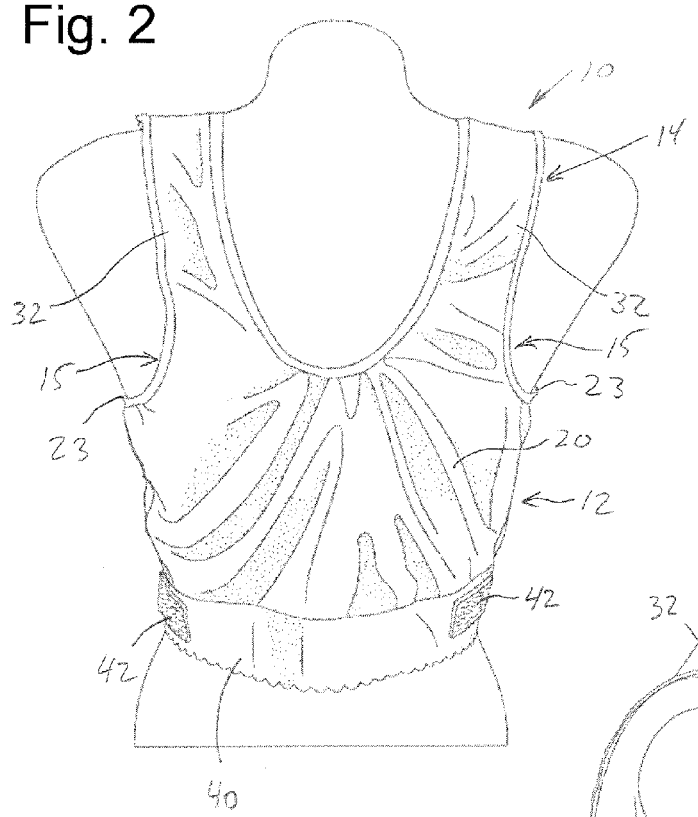
FIG. 2 is a rear perspective view of the undergarment of FIG. 1 positioned on a mannequin.
Figure 3:
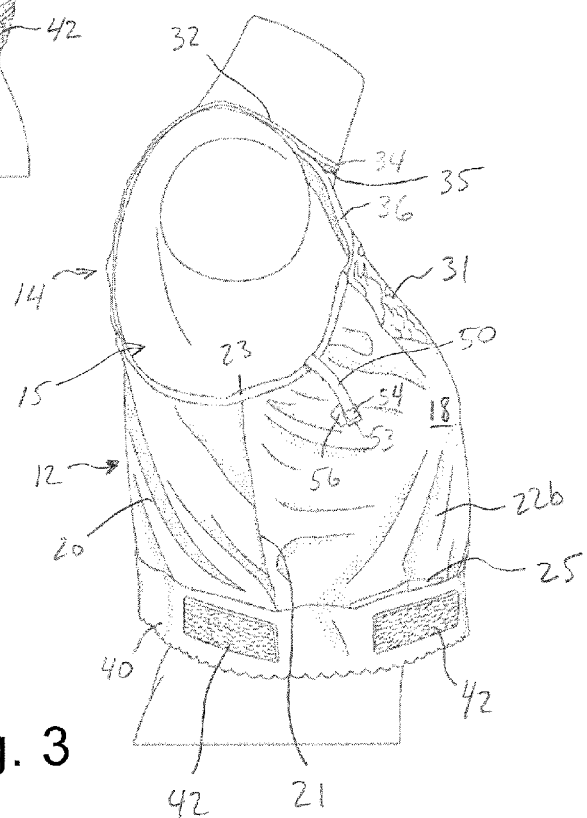
FIG. 3 is a side view of the undergarment of FIG. 1 positioned on a mannequin.
Figure 4:
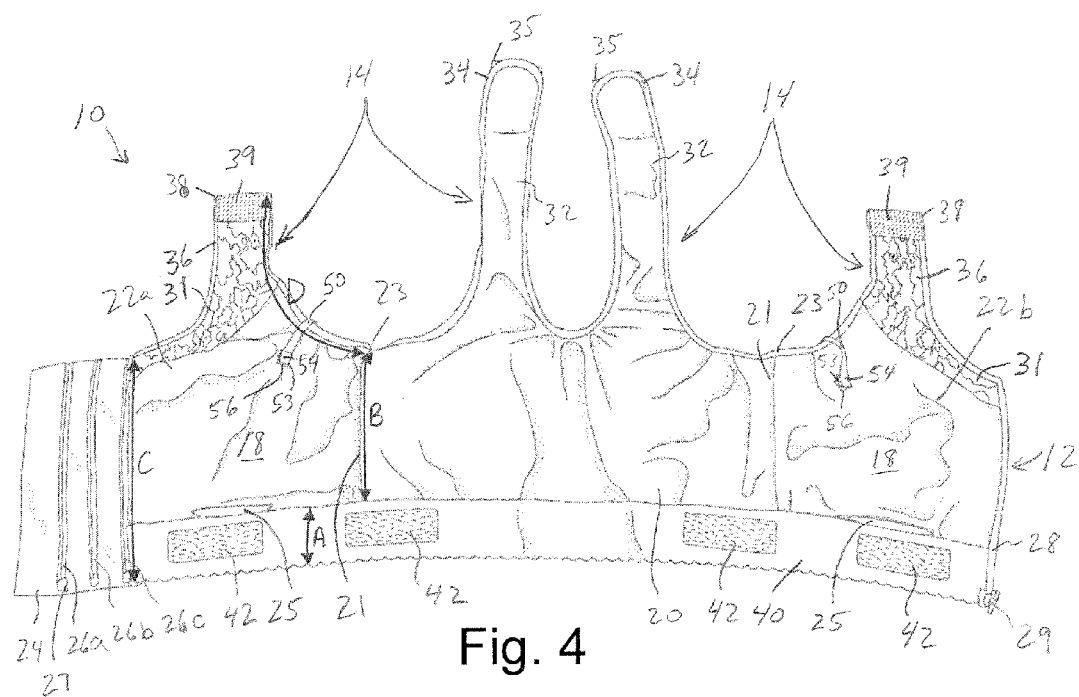
FIG. 4 is a front elevation view of the undergarment of FIG. 1.

Referring again to FIGS. 1-5, each shoulder strap 14 is defined by a rear strap portion 32 extending from the back panel 20 and a front strap portion 36 extending from a respective front panel 22a, 22b. Each rear strap portion 32 extends to a free end 34 with a connector 35 positioned thereon. Similarly, each front strap portion 36 extends to a free end 38 with a corresponding connector 39 positioned thereon. In the illustrated embodiment, the connectors 35 and 39 are complementary hook and loop fasteners, although other connectors may be utilized. With interconnectable rear and front portions 32, 36, the shoulder straps 14 are configured to open completely and close with the connectors 35, 39 to allow the wearer to easily put the undergarment 10 on and off, even with limited mobility. As illustrated in FIGS. 1-3, upon interconnection, the shoulder straps 14 define the armholes 15 with a lowermost point 23, which is typically at the seam 21 between the back panel 20 and the respective front panel 22a, 22b, although it may be otherwise positioned. In the illustrated embodiment, a decorative panel 31, for example, lace, may extend over portions of each front strap portion 36 and the respective front panels 22a, 22b. The decorative panels 31 help to take away the medical stigma and feel of a surgical bra.

The underbust band 40 extends along the length of the back panel 20 and the front panels 22a, 22b. The underbust band 40 is preferably manufactured from a material having a higher elasticity than that of the back panel 20 and front panels 22a, 22b such that the undergarment 10 is snugly secured about the wearer's abdomen. While FIG. 3 shows the band 40 positioned loosely about the abdomen, such is only for illustrative purposes of the front openings 25, which will be described hereinafter. It is intended that the band 40 will provide a snug fit about the abdomen.

While the underbust band 40 fits snugly, it is positioned and configured such that it applies minimal, if any, pressure to the wearer's incisions or tender bust area. In this regard, the underbust band 40 has a relatively large height A such that the compressive force applied thereby is distributed over a larger area. For example, the band height A is preferably 20-35% of the total height C, which is defined by the band height A+plus the panel height B at the lowermost point 23 (see FIG. 4). Most preferably, the band height is about 30% of the total height C. Additionally, the panel height B is sufficiently large such that the band 40 is positioned spaced from the bust area 18. In a preferred embodiment, the panel height B is larger than 5 inches. More preferably, the panel height B is between about 5.5 and 6.5 inches.

The configuration of the shoulder straps 14 and the main body 12 are also configured to minimize discomfort for the wearer. In this regard, the rear strap portions 32 have a racer back configuration and the front strap portions 36 have a length D from the free end 38 to the lowermost point 23 which is approximately equal to the total height C. Preferably, the ratio of the front strap length D to the total height C is between 0.95 and 1.25. With this configuration, the armhole 15 maintains sufficient room for lymph node dissection and scarring.

Figure 7:
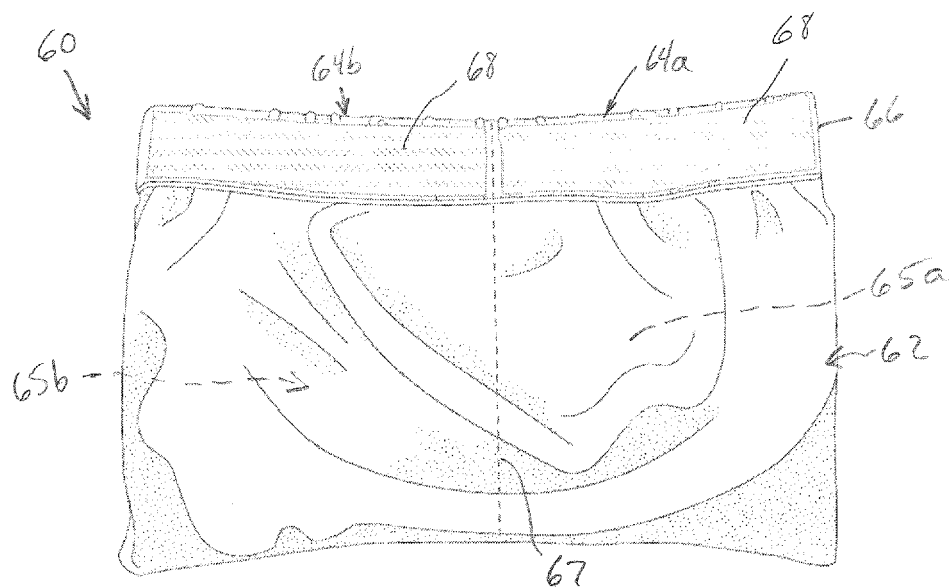
FIG. 7 is a rear elevation view of an exemplary separable pouch for use with the undergarment in accordance with the invention.

The undergarment 10 also includes several features which help to facilitate draining. Referring to FIG. 7, a pouch 60 is configured for attachment to the undergarment 10. In the illustrated embodiment, the pouch 60 includes a body 62 which is split by a seam 67 to define two pockets 65a, 65b, each with a respective opening 64a, 64b. The pockets 65a, 65b are sized to hold a respective bulb or cup (not shown). While the illustrated pouch 60 defines two pockets, the pouch 60 may be configured with more or fewer pockets. Connectors 68 extend along a portion of the pouch 60 and are configured to connect with corresponding connectors 42 positioned on the band 40. In the illustrated embodiment, the connectors 42 and 68 are complementary hook and loop fasteners, although other connectors may be utilized. It is further contemplated that one or more pouches may be permanently connected to the undergarment 10. With the connectors 42 positioned along the band 40, the weight of the bulbs/cups is not born by the main body 12 and minimizes discomfort to the wearer. The connectors 42 are preferably positioned such that the pouch 60 may be attached to either the front or the side of the undergarment.

A front opening 25 is defined along each front panel 22a, preferably at the junction between the panel 22a, 22b and the band 40. The front openings 25 facilitate easy passage of drainage tubes which may extend from incisions under the breast to a pouch 60 secured to one of the connectors 42. The openings under the breast incision area offer a way to keep the drain from pulling, while seated in the attachable drain pouch 60. For drains under the arm, a directional ribbon attachment 50 is provided on each front panel 22a, 22b and offers the wearer a way to hold the tubing in place to prevent pulling, infection, and discomfort. Each ribbon attachment 50 includes a ribbon with a fixed end 52 and a free end 54 extending to the outer surface of the respective panel 22a, 22b. The free end 54 of each ribbon includes a connector 53 configured to engage a connector 56 positioned on the respective front panel 22a, 22b. In the illustrated embodiment, the connectors 53 and 56 are complementary hook and loop fasteners, although other connectors may be utilized. It is further noted that the low, wide neckline 17 offers the wearer room for a port without interference from neckline or straps.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as defined in the claims.

What is claimed is:

1. An undergarment comprising:
  a main body including a back panel and a pair of front panels extending from opposite sides of the back panel, the front panels interconnectable to one another such that the main body defines a continuous structure;
  a pair of shoulder straps extending from an upper edge of the main body, each shoulder strap including a rear strap portion and a front strap portion which are interconnectable to one another such that the shoulder straps define an arm hole on each side of the undergarment, each armhole having a lowermost point along the main body;
  an underbust band extending along a lower edge of the main body;
  a connection placket, wherein the connection placket is connected to one of the front panels;
  a plurality of first zipper halves, wherein the plurality of first zipper halves are spaced apart upon, and supported by, the connection placket;
  a second zipper half, wherein the second zipper half is connected to the other of the front panels, and further wherein engagement of one of the plurality of first zipper halves with the second zipper half interconnects the front panels; and
  one or more pouch connectors, wherein the one or more pouch connectors extend along a surface of the underbust band.

2. The undergarment according to claim 1 wherein each front panel is connected to the back panel along a seam which is aligned with the lowermost point.

3. The undergarment according to claim 1 wherein complementary connectors extend between the front and rear strap portions.

4. The undergarment according to claim 3 wherein the complementary connectors include hook and loop fasteners.

5. The undergarment according to claim 1 wherein a decorative panel is secured along at least a portion of each front strap portion.

6. The undergarment according to claim 1 wherein the connection placket is manufactured from a material having a higher elasticity than the material of the main body.

7. The undergarment according to claim 1 wherein the underbust band is manufactured from a material having a higher elasticity than the material of the main body.

8. The undergarment according to claim 1 wherein the one or more pouch connectors extend along at least one of a front and a side location of the underbust band relative to the front panels.

9. The undergarment according to claim 1 further comprising one or more drain pouches, wherein each of the one or more drain pouches defines a chamber configured to receive a drain bulb or cup, and further wherein each of the one or more drain pouches comprises at least one connector configured for connection to the one or more pouch connectors.

10. The undergarment according to claim 1 further comprising at least one opening defined through at least one of the front panels proximate one of the pouch connectors.

11. The undergarment according to claim 1 further comprising at least one ribbon attachment secured to one of the front panels, the ribbon attachment including a ribbon with a first end connected to the front panel and a free end releasably connectable to the front panel.

12. The undergarment according to claim 1 wherein a secondary panel is secured to an inside surface of each front panel to define an inside pocket.

13. An undergarment comprising:
  a main body including a back panel and a pair of front panels extending from opposite sides of the back panel, the front panels interconnectable to one another such that the main body defines a continuous structure;
  a pair of shoulder straps extending from an upper edge of the main body, each shoulder strap defining an arm hole on each side of the undergarment;
  an underbust band extending along a lower edge of the main body with one or more pouch connectors extending therealong;
  a connection placket, wherein the connection placket is connected to one of the front panels;
  a plurality of first zipper halves, wherein the plurality of first zipper halves are spaced apart upon, and supported by, the connection placket;
  a second zipper half, wherein the second zipper half is connected to the other of the front panels, and further wherein engagement of one of the plurality of first zipper halves with the second zipper half interconnects the front panels; and
  at least one drain pouch defining a chamber configured to receive a drain bulb or cup and having a connector configured for connection to the one or more pouch connectors.

* * * * *